US009636156B2

(12) United States Patent
Black et al.

(10) Patent No.: US 9,636,156 B2
(45) Date of Patent: May 2, 2017

(54) SECURING FASTENERS

(71) Applicant: GLOBUS MEDICAL, INC., Audubon, PA (US)

(72) Inventors: Michael E. Black, Swarthmore, PA (US); Matthew Hansell, Schwenksville, PA (US); Jon Suh, Blue Bell, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 14/975,904

(22) Filed: Dec. 21, 2015

(65) Prior Publication Data

US 2016/0100868 A1    Apr. 14, 2016

Related U.S. Application Data

(63) Continuation of application No. 14/291,222, filed on May 30, 2014, now Pat. No. 9,271,774, which is a continuation of application No. 13/117,379, filed on May 27, 2011, now Pat. No. 8,771,324.

(51) Int. Cl.
*A61B 17/80* (2006.01)
*A61B 17/86* (2006.01)

(52) U.S. Cl.
CPC ...... *A61B 17/8038* (2013.01); *A61B 17/8047* (2013.01); *A61B 17/8605* (2013.01); *A61B 17/8685* (2013.01)

(58) Field of Classification Search
CPC ..... A61B 17/80; A61B 17/86; A61B 17/8038; A61B 17/8605; A61B 17/8057; A61B 17/8685

USPC .................................................. 606/280–331
See application file for complete search history.

(56) References Cited

U.S. PATENT DOCUMENTS

| | | |
|---|---|---|
| 4,484,570 A | 11/1984 | Sutter et al. |
| 5,275,601 A | 1/1994 | Gogolewski et al. |
| 5,616,142 A | 4/1997 | Yuan et al. |
| 5,700,263 A | 12/1997 | Schendel |
| 5,735,853 A | 4/1998 | Olerud |
| 5,741,268 A | 4/1998 | Schutz |
| 5,827,286 A | 10/1998 | Incavo et al. |
| 5,827,290 A | 10/1998 | Bradley |
| 5,931,838 A | 8/1999 | Vito |
| 6,030,389 A | 2/2000 | Wagner et al. |
| 6,030,740 A | 2/2000 | Polykarpov |
| 6,139,550 A | 10/2000 | Michelson |
| 6,183,476 B1 | 2/2001 | Gerhardt et al. |
| 6,193,721 B1 | 2/2001 | Michelson |
| 6,235,033 B1 | 5/2001 | Brace et al. |
| 6,241,731 B1 | 6/2001 | Fiz |
| 6,261,291 B1 | 7/2001 | Talaber et al. |
| 6,273,893 B1 | 8/2001 | McAllen, III et al. |
| 6,306,136 B1 | 10/2001 | Baccelli |
| 6,328,738 B1 | 12/2001 | Suddaby |

(Continued)

*Primary Examiner* — Christopher Beccia

(57) ABSTRACT

A fastener, for example a bone screw, is sized to pass into an aperture of an implant, for example, a bone plate, the fastener having an anchor portion engageable with body tissue, and a head portion formed by an assembly of an insert and an anchor extension. The insert and anchor extension cooperate to form a reduced dimension passable into the aperture, and an expanded dimension not passable out of the aperture. The size of the assembly may be configurable, for example, by tabs, ramped surfaces, or an expanding diameter of a threadable insert.

20 Claims, 4 Drawing Sheets

(56) References Cited

U.S. PATENT DOCUMENTS

| | | |
|---|---|---|
| 6,331,179 B1 | 12/2001 | Freid et al. |
| 6,361,537 B1 | 3/2002 | Anderson |
| 6,370,993 B1 | 4/2002 | Pitstick |
| 6,383,186 B1 | 5/2002 | Michelson |
| 6,398,783 B1 | 6/2002 | Michelson |
| 6,402,755 B1 | 6/2002 | Pisharodi |
| 6,402,759 B1 | 6/2002 | Strong et al. |
| 6,428,542 B1 | 8/2002 | Michelson |
| 6,454,769 B2 | 9/2002 | Wagner et al. |
| 6,454,771 B1 | 9/2002 | Michelson |
| 6,554,834 B1 | 4/2003 | Crozet et al. |
| 6,575,975 B2 | 6/2003 | Brace et al. |
| 6,592,586 B1 | 7/2003 | Michelson |
| 6,599,290 B2 | 7/2003 | Bailey et al. |
| 6,602,255 B1 | 8/2003 | Campbell et al. |
| 6,605,090 B1 | 8/2003 | Trieu et al. |
| 6,613,053 B1 | 9/2003 | Collins et al. |
| 6,626,907 B2 | 9/2003 | Blain et al. |
| 6,645,208 B2 | 11/2003 | Apfelbaum et al. |
| 6,679,883 B2 | 1/2004 | Hawkes et al. |
| 6,689,134 B2 | 2/2004 | Ralph et al. |
| 6,695,677 B1 | 2/2004 | Lin |
| 6,695,848 B2 | 2/2004 | Haines |
| 6,702,817 B2 | 3/2004 | Beger et al. |
| 6,702,836 B2 | 3/2004 | Fuhr |
| 6,712,818 B1 | 3/2004 | Michelson |
| 6,719,759 B2 | 4/2004 | Wagner et al. |
| 6,743,255 B2 | 6/2004 | Ferree |
| 6,852,113 B2 | 2/2005 | Nathanson et al. |
| 6,855,147 B2 | 2/2005 | Harrington, Jr. |
| 6,890,334 B2 | 5/2005 | Brace et al. |
| 6,932,820 B2 | 8/2005 | Osman |
| 6,936,050 B2 | 8/2005 | Michelson |
| 6,945,973 B2 | 9/2005 | Bray |
| 6,964,664 B2 | 11/2005 | Freid et al. |
| 7,001,389 B1 | 2/2006 | Navarro et al. |
| 7,008,426 B2 | 3/2006 | Paul |
| 7,008,427 B2 | 3/2006 | Sevrain |
| 7,041,105 B2 | 5/2006 | Michelson |
| 7,044,952 B2 | 5/2006 | Michelson |
| 7,070,599 B2 | 7/2006 | Paul |
| 7,070,601 B2 | 7/2006 | Culbert et al. |
| 7,074,221 B2 | 7/2006 | Michelson |
| 7,077,843 B2 | 7/2006 | Thramann et al. |
| 7,077,844 B2 | 7/2006 | Michelson |
| 7,094,239 B1 | 8/2006 | Michelson |
| 7,097,645 B2 | 8/2006 | Michelson |
| 7,112,202 B2 | 9/2006 | Michelson |
| 7,115,130 B2 | 10/2006 | Michelson |
| 7,118,573 B2 | 10/2006 | Michelson |
| 7,162,939 B2 | 1/2007 | Totsu |
| 7,175,623 B2 | 2/2007 | Thramann et al. |
| 7,179,260 B2 | 2/2007 | Gerlach et al. |
| 7,186,254 B2 | 3/2007 | Dinh et al. |
| 7,186,255 B2 | 3/2007 | Baynham et al. |
| 7,186,256 B2 | 3/2007 | Michelson |
| 7,195,633 B2 | 3/2007 | Medoff et al. |
| 7,214,226 B2 | 5/2007 | Alleyne |
| 7,229,443 B2 | 6/2007 | Eberlein et al. |
| 7,255,699 B2 | 8/2007 | Paul |
| 7,311,712 B2 | 12/2007 | Dalton |
| 7,318,825 B2 | 1/2008 | Butler et al. |
| 7,326,212 B2 | 2/2008 | Huebner |
| 7,331,961 B2 | 2/2008 | Abdou |
| 7,399,301 B2 | 7/2008 | Michelson |
| 7,419,499 B2 | 9/2008 | Dalton |
| 7,452,370 B2 | 11/2008 | Anderson |
| 7,481,811 B2 | 1/2009 | Suh |
| 7,534,325 B2 | 5/2009 | Quigley et al. |
| 7,547,306 B2 | 6/2009 | Michelson |
| 7,575,623 B2 | 8/2009 | Boll et al. |
| 7,611,527 B2 | 11/2009 | Freid et al. |
| 7,625,381 B2 | 12/2009 | Michelson |
| 7,635,364 B2 | 12/2009 | Barrall et al. |
| 7,635,366 B2 | 12/2009 | Abdou |
| 7,637,928 B2 | 12/2009 | Fernandez |
| 7,645,295 B2 | 1/2010 | Osman |
| 7,651,497 B2 | 1/2010 | Michelson |
| 7,682,379 B2 | 3/2010 | Mathieu et al. |
| 7,708,739 B2 | 5/2010 | Kilburn et al. |
| 7,727,265 B2 | 6/2010 | Paul |
| 7,763,056 B2 | 7/2010 | Dalton |
| 7,766,947 B2 | 8/2010 | Hawkes et al. |
| 7,780,666 B1 | 8/2010 | Navarro et al. |
| 7,785,327 B1 | 8/2010 | Navarro et al. |
| 7,794,482 B2 | 9/2010 | Mathieu et al. |
| 7,846,163 B2 | 12/2010 | Fourcault et al. |
| 7,846,190 B2 | 12/2010 | Ball |
| 7,857,839 B2 | 12/2010 | Duong et al. |
| 7,935,137 B2 | 5/2011 | Gorhan et al. |
| 7,981,142 B2 | 7/2011 | Konieczynski et al. |
| 8,152,838 B2 | 4/2012 | Ensign et al. |
| 8,211,154 B2 * | 7/2012 | Fisher ................ A61B 17/8047 606/289 |
| 8,241,339 B2 | 8/2012 | Suh et al. |
| 8,652,183 B1 * | 2/2014 | Truman ............ A61B 17/8038 606/281 |
| 2002/0058893 A1 | 5/2002 | Vesey |
| 2002/0156474 A1 | 10/2002 | Wack et al. |
| 2003/0105462 A1 | 6/2003 | Haider |
| 2003/0187440 A1 | 10/2003 | Richelsoph et al. |
| 2003/0187509 A1 | 10/2003 | Lemole, Jr. |
| 2003/0229348 A1 | 12/2003 | Sevrain |
| 2004/0006343 A1 | 1/2004 | Sevrain |
| 2004/0019353 A1 | 1/2004 | Freid et al. |
| 2004/0092939 A1 | 5/2004 | Freid et al. |
| 2004/0097935 A1 | 5/2004 | Richelsoph et al. |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0153069 A1 | 8/2004 | Paul |
| 2004/0204712 A1 | 10/2004 | Kolb et al. |
| 2004/0236334 A1 | 11/2004 | Michelson |
| 2005/0010227 A1 | 1/2005 | Paul |
| 2005/0021032 A1 | 1/2005 | Koo |
| 2005/0049593 A1 | 3/2005 | Duong et al. |
| 2005/0049595 A1 | 3/2005 | Suh et al. |
| 2005/0059970 A1 | 3/2005 | Kolb |
| 2005/0059971 A1 | 3/2005 | Michelson |
| 2005/0107796 A1 | 5/2005 | Gerlach et al. |
| 2005/0149026 A1 | 7/2005 | Butler et al. |
| 2005/0182404 A1 | 8/2005 | Lauryssen et al. |
| 2005/0187551 A1 | 8/2005 | Orbay et al. |
| 2005/0192577 A1 | 9/2005 | Mosca et al. |
| 2005/0192580 A1 | 9/2005 | Dalton |
| 2005/0228386 A1 | 10/2005 | Ziolo et al. |
| 2005/0234455 A1 | 10/2005 | Binder et al. |
| 2005/0273105 A1 | 12/2005 | Konieczynski et al. |
| 2005/0277937 A1 | 12/2005 | Leung et al. |
| 2005/0283152 A1 | 12/2005 | Lindemann et al. |
| 2006/0009770 A1 | 1/2006 | Speirs et al. |
| 2006/0058797 A1 | 3/2006 | Mathieu et al. |
| 2006/0100626 A1 | 5/2006 | Rathbun et al. |
| 2006/0116678 A1 | 6/2006 | Impellizzeri |
| 2006/0122604 A1 * | 6/2006 | Gorhan ............ A61B 17/8038 606/86 B |
| 2006/0122605 A1 | 6/2006 | Suh et al. |
| 2006/0142768 A1 | 6/2006 | Paul |
| 2006/0149251 A1 | 7/2006 | Ziolo et al. |
| 2006/0149256 A1 | 7/2006 | Wagner et al. |
| 2006/0149264 A1 | 7/2006 | Castaneda et al. |
| 2006/0161157 A1 | 7/2006 | Mosca et al. |
| 2006/0167456 A1 * | 7/2006 | Johnston ............ A61B 17/1728 606/86 B |
| 2006/0195100 A1 | 8/2006 | Kirschman |
| 2006/0200134 A1 | 9/2006 | Freid et al. |
| 2006/0200147 A1 | 9/2006 | Ensign et al. |
| 2006/0235399 A1 | 10/2006 | Carls et al. |
| 2006/0235405 A1 | 10/2006 | Hawkes |
| 2006/0241612 A1 | 10/2006 | Medoff |
| 2006/0241616 A1 | 10/2006 | Konieczynski et al. |
| 2006/0264936 A1 * | 11/2006 | Partin ................ A61B 17/683 606/281 |
| 2006/0271052 A1 | 11/2006 | Stern |

(56) References Cited

U.S. PATENT DOCUMENTS

| | | |
|---|---|---|
| 2006/0276793 A1 | 12/2006 | Berry |
| 2006/0276794 A1 | 12/2006 | Stern |
| 2007/0016206 A1 | 1/2007 | Thramann et al. |
| 2007/0021476 A1 | 1/2007 | Jaquith et al. |
| 2007/0033437 A1 | 2/2007 | Kawamura et al. |
| 2007/0118125 A1 | 5/2007 | Orbay et al. |
| 2007/0118126 A1 | 5/2007 | Medoff et al. |
| 2007/0123884 A1 | 5/2007 | Abdou |
| 2007/0162020 A1 | 7/2007 | Gerlach et al. |
| 2007/0213729 A1 | 9/2007 | Lindemann et al. |
| 2007/0233120 A1 | 10/2007 | Thramann et al. |
| 2007/0270855 A1 | 11/2007 | Partin |
| 2007/0288010 A1 | 12/2007 | Alleyne |
| 2008/0065070 A1 | 3/2008 | Freid et al. |
| 2008/0097445 A1 | 4/2008 | Weinstein |
| 2008/0108998 A1 | 5/2008 | Lindemann |
| 2008/0114361 A1 | 5/2008 | Butler et al. |
| 2008/0132960 A1 | 6/2008 | Weaver et al. |
| 2008/0140130 A1 | 6/2008 | Chan et al. |
| 2008/0154312 A1 | 6/2008 | Colleran et al. |
| 2008/0177263 A1 | 7/2008 | Freedman et al. |
| 2008/0177330 A1 | 7/2008 | Ralph et al. |
| 2008/0188899 A1 | 8/2008 | Bottlang et al. |
| 2008/0195100 A1 | 8/2008 | Capote et al. |
| 2008/0234680 A1 | 9/2008 | Zaiser et al. |
| 2008/0234750 A1 | 9/2008 | Woods et al. |
| 2008/0243191 A1 | 10/2008 | Tipirneni et al. |
| 2008/0243192 A1 | 10/2008 | Jacene et al. |
| 2008/0269753 A1 | 10/2008 | Cannestra |
| 2008/0269768 A1 | 10/2008 | Schwager et al. |
| 2008/0269807 A1 | 10/2008 | Simon et al. |
| 2008/0275510 A1 | 11/2008 | Schonhardt et al. |
| 2008/0287999 A1 | 11/2008 | Markworth |
| 2008/0288000 A1 | 11/2008 | Cawley |
| 2008/0288001 A1 | 11/2008 | Cawley et al. |
| 2008/0300637 A1 | 12/2008 | Austin et al. |
| 2009/0012571 A1 | 1/2009 | Perrow et al. |
| 2009/0018557 A1 | 1/2009 | Pisharodi |
| 2009/0024170 A1 | 1/2009 | Kirschman |
| 2009/0036933 A1 | 2/2009 | Dube et al. |
| 2009/0054930 A1 | 2/2009 | Aflatoon |
| 2009/0062862 A1 | 3/2009 | Perrow et al. |
| 2009/0076509 A1 | 3/2009 | Bush, Jr. et al. |
| 2009/0082813 A1 | 3/2009 | Long et al. |
| 2009/0088807 A1 | 4/2009 | Castaneda et al. |
| 2009/0118773 A1 | 5/2009 | James et al. |
| 2009/0131988 A1 | 5/2009 | Bush, Jr. et al. |
| 2009/0143824 A1 | 6/2009 | Austin et al. |
| 2009/0182383 A1 | 7/2009 | Prybyla et al. |
| 2009/0216282 A1 | 8/2009 | Blake et al. |
| 2009/0222051 A1 | 9/2009 | Pengo |
| 2009/0248087 A1 | 10/2009 | Lewis et al. |
| 2009/0259226 A1 | 10/2009 | Michelson |
| 2009/0264934 A1 | 10/2009 | Youssef et al. |
| 2009/0287257 A1 | 11/2009 | Hagen |
| 2009/0312803 A1 | 12/2009 | Austin et al. |
| 2009/0318978 A1 | 12/2009 | Podgorski et al. |
| 2010/0057138 A1 | 3/2010 | Murner et al. |
| 2010/0063505 A1 | 3/2010 | Frigg et al. |
| 2010/0069969 A1 | 3/2010 | Ampuero et al. |
| 2010/0076495 A1 | 3/2010 | Lindemann et al. |
| 2010/0076496 A1 | 3/2010 | Fernandez |
| 2010/0082029 A1 | 4/2010 | Ibrahim et al. |
| 2010/0114176 A1 | 5/2010 | Ibrahim et al. |
| 2010/0121329 A1 | 5/2010 | Ryan et al. |
| 2010/0137909 A1 | 6/2010 | Osman |
| 2010/0179559 A1 | 7/2010 | Walker |
| 2010/0211108 A1 | 8/2010 | Lemole, Jr. |
| 2010/0211116 A1 | 8/2010 | Suh et al. |
| 2010/0222827 A1 | 9/2010 | Griffiths et al. |
| 2010/0234888 A1 | 9/2010 | McClintock et al. |
| 2010/0256686 A1 | 10/2010 | Fisher et al. |
| 2010/0274294 A1 | 10/2010 | Biedermann et al. |
| 2010/0324604 A1 | 12/2010 | Mathieu et al. |
| 2011/0098715 A1 | 4/2011 | Laubert et al. |
| 2011/0172719 A1 | 7/2011 | Gorhan et al. |
| 2011/0270326 A1 | 11/2011 | Black et al. |
| 2012/0179207 A1 | 7/2012 | Mekhail et al. |
| 2013/0096633 A1 | 4/2013 | Black et al. |
| 2013/0129447 A1 | 5/2013 | Canizares, Jr. et al. |

* cited by examiner

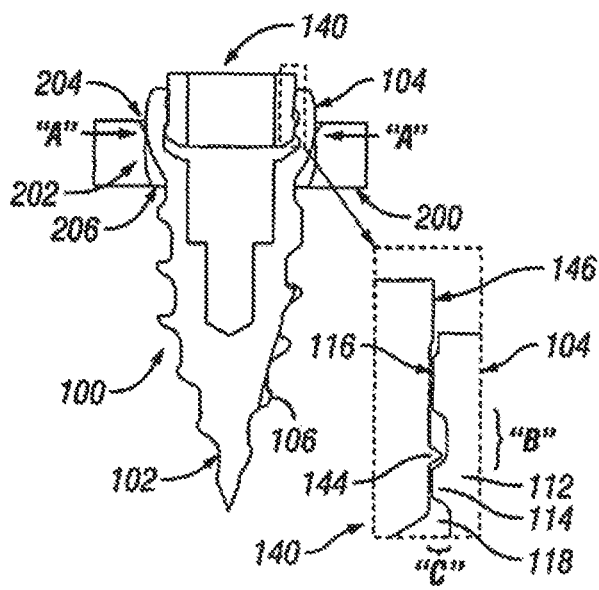
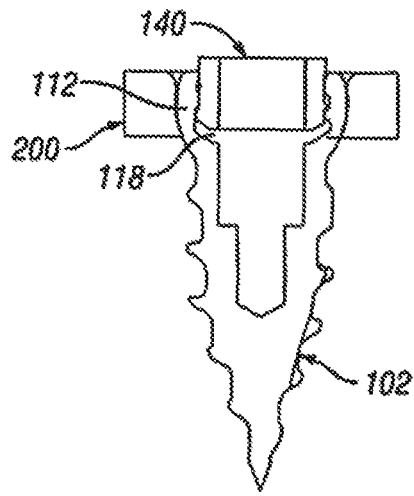
FIG. 1  FIG. 1A  FIG. 2
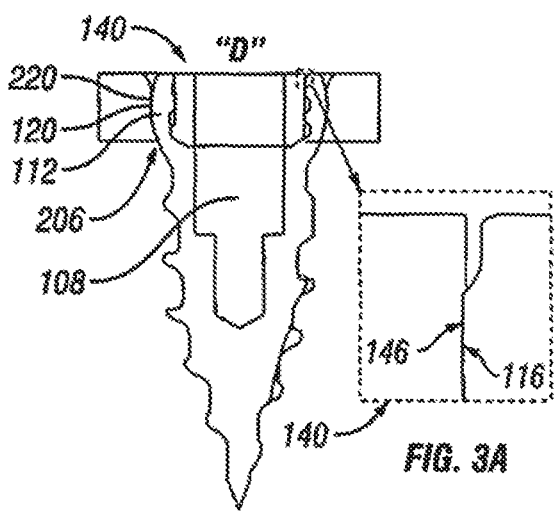
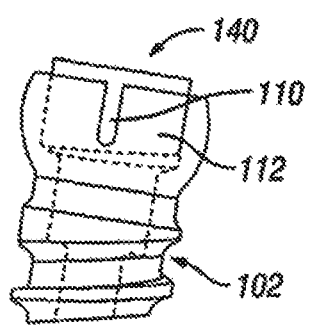
FIG. 3  FIG. 3A  FIG. 4
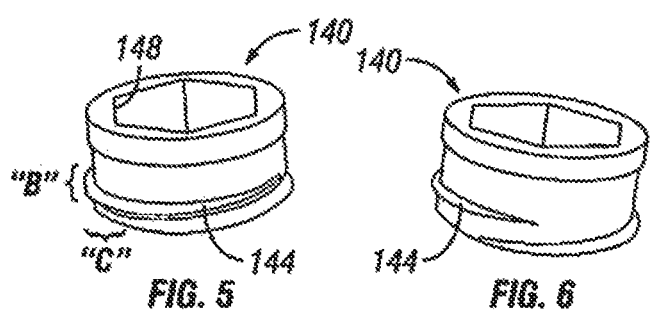
FIG. 5  FIG. 6

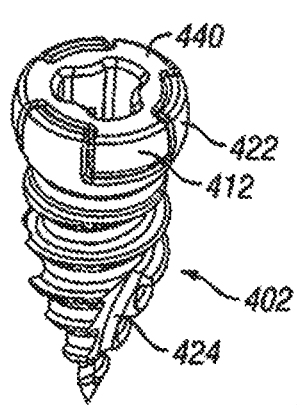
FIG. 13
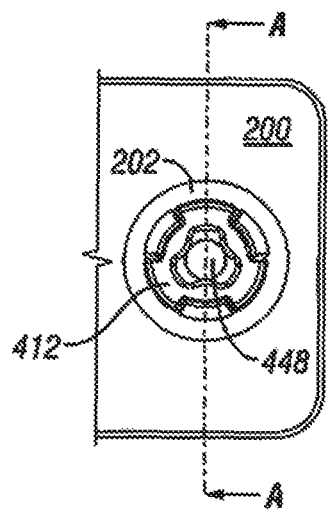
FIG. 14
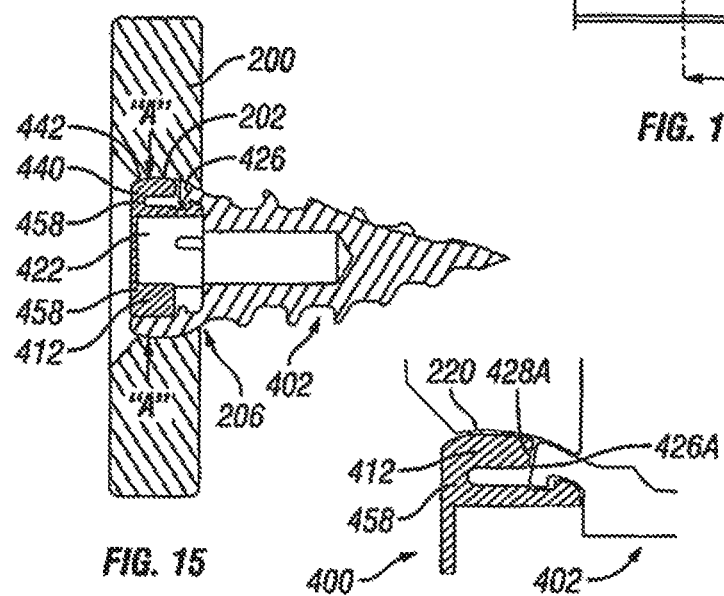
FIG. 15
FIG. 15A
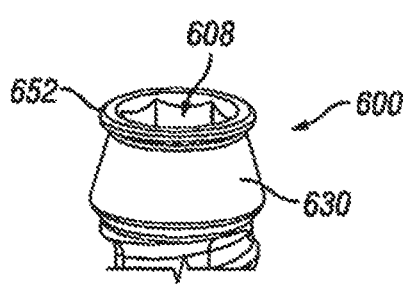
FIG. 16
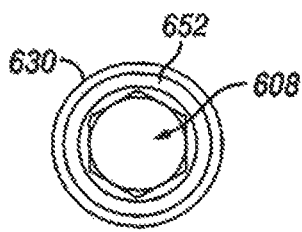
FIG. 17
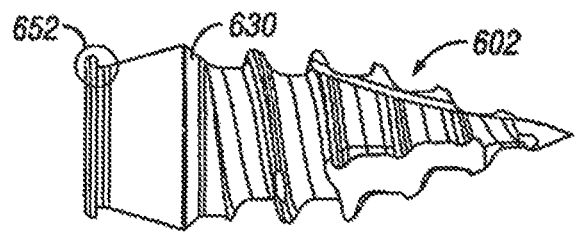
FIG. 18

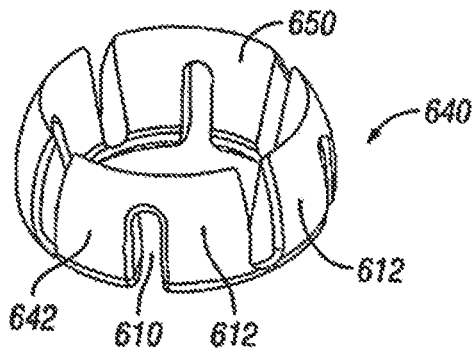
FIG. 19
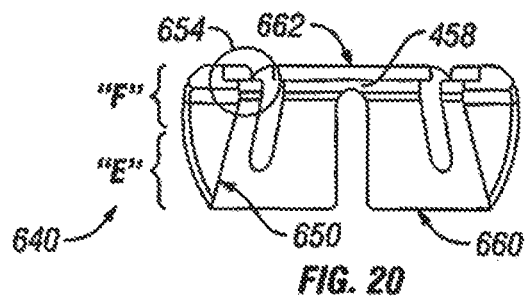
FIG. 20
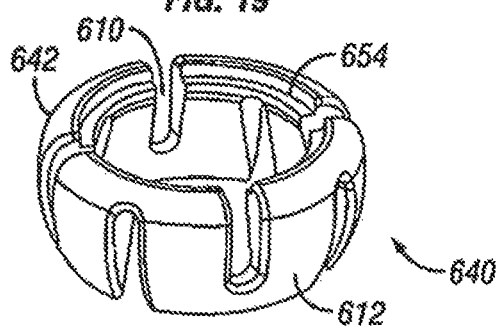
FIG. 21
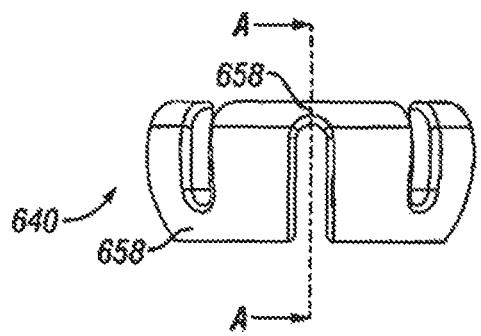
FIG. 22
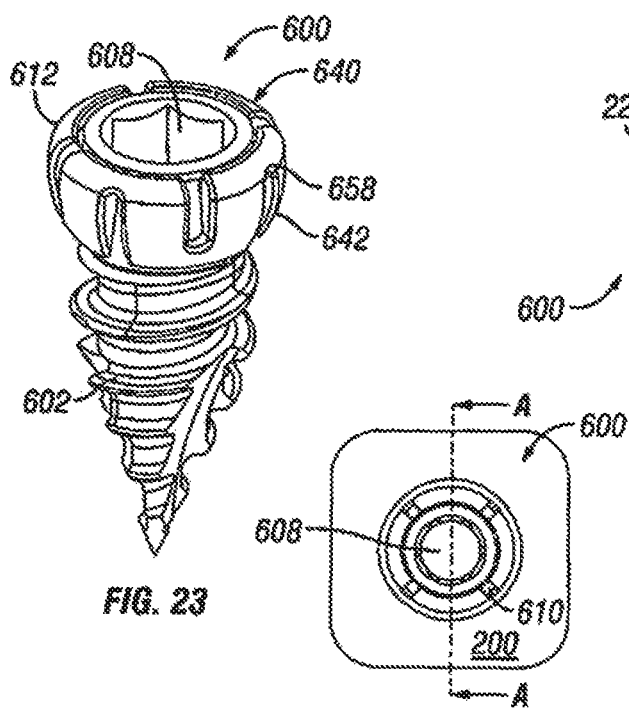
FIG. 23
FIG. 24
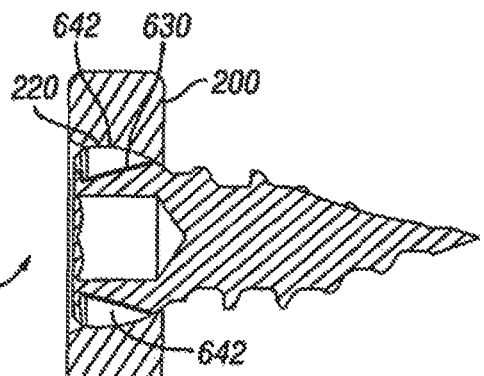
FIG. 25

US 9,636,156 B2

SECURING FASTENERS

CROSS-REFERENCE TO RELATED APPLICATIONS

This application is a continuation of U.S. patent application Ser. No. 14/291,222, filed May 30, 2014, which is a continuation of U.S. patent application Ser. No. 13/117,379, filed May 27, 2011, now U.S. Pat. No. 8,771,324. These applications are incorporated by reference herein in their entireties for all purposes.

FIELD OF THE INVENTION

The invention relates to bone fixation, and more particularly to securing polyaxial bone screws within an implant.

BACKGROUND OF THE INVENTION

Bones may be reinforced with rigid structures, for example plates, having apertures through which bone screws, for example polyaxial screws, may pass. Such reinforcing is useful for addressing fractures or other trauma, correcting alignment, or treating disease. A bone plate is used to span a fracture, or to join different bones. It is important that a bone screw securing a bone plate does not loosen and separate from the plate postoperatively. This separation or backing out may be a result of the screws failure to achieve a sufficient purchase in the bone, although the stripping of the screws has also been known to cause this problem, or can be a result of the forces placed upon the screws from spinal movement. Regardless of the cause of the hardware failures, a surgeon must repair or replace the broken or separated parts, requiring an undesirable invasive procedure.

Devices for preventing this separation may be associated with the plate or screw. Examples include a cover positioned over all or part of the screw head, or an expansion head screw.

SUMMARY OF THE INVENTION

An embodiment of a fastener for securing body tissue relative to an implant, the implant having an aperture with a narrowed entry portion, comprises an anchor portion configured for passing through the aperture and attaching to body tissue; a head portion including an anchor extension and an insert engageable with the anchor extension, the head having a plurality of resilient tabs disposed on the anchor extension and/or the insert and forming a first dimension sized larger than a dimension of the narrowed entry portion, the plurality of resilient tabs bendable to form a second reduced dimension relative to the first dimension, the head portion passable past the narrowed entry portion and into the aperture when the tabs form the second dimension, and at least one ramp configured to contact the plurality of resilient tabs and to thereby prevent bending of the plurality of resilient tabs to form the second reduced dimension after the head portion has been passed past the narrowed entry portion into the aperture, the head portion thereby prevented from passing back out of the aperture.

In variations of the embodiment, the insert and the anchor extension are configured to mutually engage; the mutual engagement includes a first flange on one of the anchor extension or insert, and a second bendable flange on the other of the anchor extension or insert, the second flange operable when bent to pass over or under the first flange and thereafter to resume an unbent configuration thereby forming an engagement between the first and second flanges; the insert and the anchor extension are mutually engaged prior to the head portion being passed into the aperture; the anchor extension and the insert form a curved exterior surface when mutually assembled, the curved surface pivotably engageable with a curved surface inside the aperture; and the tabs are formed by reliefs disposed between successive tabs, the reliefs forming hinged portions from which the plurality of tabs extend.

In yet further variations, the ramp is configured to bend the plurality of resilient tabs to form a third dimension at least as large as the first dimension; the anchor extension or the insert include a tool engagement profile operative to be engaged by a tool for driving the fastener into body tissue; and the engagement profile forms three primary faces.

In a further embodiment, the fastener further includes a threadable engagement between the insert and the anchor extension, the threadable engagement operative to bend the plurality of resilient tabs to form a dimension at least as large as the first dimension. In another embodiment, the anchor extension includes a ramp, the insert includes a ramp, and the anchor extension ramp and the insert ramp mutually engage when the anchor portion is moved in a direction back through the aperture to cooperatively increase a dimension of the head portion.

In yet further embodiments, the cooperative engagement causes the insert to expand in diameter; the plurality of resilient tabs are disposed upon the insert, the insert passable through the narrowed entry portion into the aperture in a first direction using a first insertion force, and passable out of the narrowed entry portion in a second direction with a second force substantially greater than the first force, the insert engageable with the anchor extension to cause the anchor extension to be passable out of the aperture in the second direction only by application of a force at least as great as the second force.

In other embodiments, the at least one ramp is disposed open to each of the plurality of resilient tabs, the at least one ramp operative to engage the narrowed entry portion when the fastener is passed into the aperture to thereby bend the resilient tabs; and, the insert is an expandable ring including the resilient tabs.

An embodiment forming a system for securing body tissue comprises an implant having an aperture with a narrowed entry portion; and a fastener having an anchor portion configured for passing through the aperture and attaching to body tissue; and a head portion including an anchor extension and an insert engageable with the anchor extension, the head having a plurality of resilient tabs disposed on the anchor extension and or the insert and forming a first dimension sized larger than a dimension of the narrowed entry portion, the plurality of resilient tabs bendable to form a second reduced dimension relative to the first dimension, the head portion passable past the narrowed entry portion and into the aperture when the tabs form the second dimension, and at least one ramp configured to contact the plurality of resilient tabs and to thereby prevent bending of the plurality of resilient tabs to form the second reduced dimension after the head portion has been passed past the narrowed entry portion into the aperture, the head portion thereby prevented from passing back out of the aperture.

In a variation, the at least one ramp is formed upon the insert, and the aperture includes a ramped interior surface cooperative with the at least one ramp formed upon the insert to form a close conforming pivotable connection between the implant and the fastener; and, the implant forms a vertebral plate and the fastener forms a bone screw.

A method of securing body tissue relative to an implant, the implant having an aperture with a narrowed entry portion, comprises passing an anchor portion of a fastener through the aperture; attaching the anchor portion to body tissue; engaging an insert with the anchor portion to form a head having a plurality of resilient tabs, the head forming a first dimension sized larger than a dimension of the narrowed entry portion; bending the plurality of resilient tabs to form a second reduced dimension relative to the first dimension, and passing the head portion past the narrowed entry portion and into the aperture; and releasing the resilient tabs to form a dimension at least as large as the first dimension, wherein the fastener is secured within the aperture. In a variation, a further step includes sliding a ramp of the fastener along the narrowed entry portion to bend the plurality of resilient tabs.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 depicts a cross-section of a fastener with an anchor extension having bendable tabs, and an internally disposed insert, the fastener position prior to passage past a narrowed portion of an aperture in an implant;

FIG. 1A depicts an enlarged view of an indicated region of the fastener of FIG. 1;

FIG. 2 depicts the fastener of FIG. 1 inserted into the aperture, an insert not yet fully threaded into engagement with the anchor extension;

FIG. 3 depicts the fastener of FIG. 1, the insert fully threaded into engagement with the anchor extension;

FIG. 3A depicts an enlarged view of an indicated region of the fastener of FIG. 3;

FIG. 4 depicts a perspective view of the fastener of FIG. 1, including an insert not fully engaged;

FIGS. 5-6 depict perspective views of the insert of FIG. 1;

FIG. 13 depicts a perspective view of the fastener of FIG. 9, assembled together with the insert of FIG. 10;

FIG. 14 depicts the assembly of FIG. 13 assembled into an implant;

FIG. 15 depicts a cross sectional side view of the assembly of FIG. 14;

FIG. 15A is an enlarged view of a portion of FIG. 15, illustrating an alternative configuration;

FIG. 16 is a perspective view of an alternative anchor extension;

FIG. 17 is a top view of the anchor extension of FIG. 16;

FIG. 18 is a side view of a fastener including the anchor extension of FIG. 16;

FIG. 19 is a perspective view of an insert;

FIG. 20 is a side view of the insert of FIG. 19;

FIG. 21 is a perspective view of an upper side of the insert of FIG. 19;

FIG. 22 is a side view of the insert of FIG. 19;

FIG. 23 is a perspective view of the fastener of FIG. 18 assembled with the insert of FIG. 19;

FIG. 24 is a top view of the assembly of FIG. 23 assembled into an implant; and

FIG. 25 is a cross sectional side view of the assembly of FIG. 24.

DETAILED DESCRIPTION OF THE INVENTION

Figure 7:
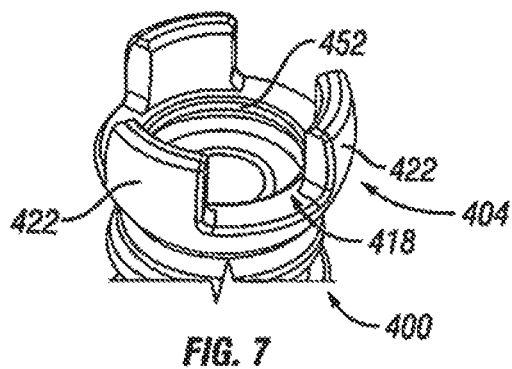
FIG. 7 depicts a perspective view of an anchor extension.

In the description which follows, any reference to direction or orientation is intended primarily and solely for purposes of illustration and is not intended in any way as a limitation to the scope of the present invention. Also, the particular embodiments described herein are not to be considered as limiting of the present invention.

One-step locking screw embodiments are disclosed, advantageously utilized with an implant, for example a joining member such as a plate having a fastener or screw aperture, though which an anchor portion of a fastener may pass, but not the fastener head. The reduced number of surgical steps needed to install the disclosed plates and fasteners advantageously reduces the overall time and complexity of the surgery, while enabling polyaxial fastener orientation.

The term "backing out" or "back out" herein refers to movement of a fastener of the disclosure from a position inserted within body tissue, along a direction reversed with respect to a direction of insertion, whereupon the fastener may be caused to exhibit a reduced fastening effect. Back out may be caused by micromotion; disease including tissue degradation; trauma; or other cause.

Turning now to the drawings, in which like reference numerals refer to like elements, FIG. 1 shows one embodiment of a fastener 100 including an anchor 102 portion which engages body tissue, and a head 104 portion extending from anchor 102 which engages a mating implant 200, having an aperture 202. In one embodiment, implant 200 is a plate securable to one or more bones or bone portions, for example vertebrae, in order to maintain the bones in a desired relative orientation for therapeutic benefit of a patient. Implant 200 is provided with an insertion end, through which a fastener of the disclosure is inserted, and an exit 206 through which a portion of the fastener may extend, but which is sized too small to prevent passage of head 104.

Implant 200 may have any shape or purpose, and may include, for example, plates, rods, bars, joint replacements, or other anchoring members, and may be used to join body tissues anywhere in the body. Applications for the instant disclosure include stabilizing any vertebrae, for example cervical, thoracic, or lumbar vertebrae; joining bone fractures; joining soft tissue, for example tendons or ligaments, to bone; or any procedure hereinafter developed, which advantageously benefits from a reliable anchor connection, and particularly for a polyaxial screw anchor connection.

To engage fastener 100 to implant 200, anchor 102 is passed through an aperture 202 in implant 200, by any known or hereinafter devised means. For example, anchor 102 may be passed into a preformed opening in body tissue, or may form or expand an opening in body tissue by self drilling and or self tapping. Threads 106 are advantageously provided to engage body tissue, for example cortical bone, cancellous bone, tendinous, ligamentous, or other body tissue capable of being securely engaged by threads. Alternatively, a separate fastener, not shown, for example a nut, may engage anchor 102. In accordance with this disclosure, any number of fasteners 100 may be passed through any number of apertures 202, in any number of implants 200. Head 104 is provided with tool engagement means, for example a Phillips, hex, or other engagement profile 108, whereby a tool may be used to position and or drive fastener 100 into engagement with implant 200 and or body tissue.

Fastener head 104 is configured to change a dimension from a first resting maximum dimension to a second expanded maximum dimension. Head 104 is further sized and dimensioned to be passable at least in part into aperture 202. Fastener head 104 is further configured to form a compressed dimension which is advantageously sized to be passable through a minimum dimension at an entrance 204 of aperture 202, but too large to be passable through an exit 206 of aperture 202. In this manner, fastener 100 may securely connect implant 200 relative to a body when anchor 102 is engaged with tissue of the body. In FIG. 1, a confluence of a resting dimension of head 104 and a minimal dimension of aperture 202 are indicated by arrows "A". Entrance 204 is advantageously chamfered to facilitate entry of fastener 100 into implant 200. Plate 200 additionally includes a reduced dimension located on an opposite side to an entrance 204, at an exit 206 to implant 200, operative to prevent fastener heads of the embodiments herein from passing through implant 200.

Head 104 is configured to change from a resting maximum dimension to an expanded maximum dimension by being provided with one or more reliefs 110, one of which is visible in FIG. 4. In one embodiment, head 104 forms an increased diameter in an expanded maximum dimension. In the embodiment of FIGS. 1-6, a threaded insert 140 is sized and dimensioned to be passed into an opening in head 104, and to thereby expand head 104 from the resting maximum dimension to the expanded maximum dimension. Insert 140 includes an increasing diameter from a leading end to a trailing end, and thereby operates to expand head 104 during its introduction thereinto. The increasing diameter may be associated with a ramping or increase in a core or body of insert 140, or an increase in thread height, as more fully described below.

Reliefs 110 divide head 104 into separate tabs 112 which, due to the reliefs 110, may more easily resiliently bend and deflect radially outwards from an axial center of fastener 100, and thereby increase a maximum dimension of head 104 to a dimension at least as large as the resting maximum dimension, and advantageously substantially larger than said resting maximum dimension.

With reference in particular to enlarged view FIG. 1A, head 104 is provided with threads 114 which cooperate with threads 144 of insert 140. Insert 140 may be preassembled by being partially threaded into head 104 as part of a manufacturing process, prior to surgery, or in the operating theatre. When fastener 100 has been inserted and head 104 has been positioned within aperture 202, insert 140 may be rotated to expand head 104, and to thereby fixedly bind head 104 in a set position within aperture 202.

It is advantageous for the thread pitch of threads 114 and 144 to be substantially the same, although where sufficient expansion may be achieved through a limited amount of rotation, this is not always a requirement. In addition to an expanding diameter, a thickness of threads 114 and or 144 may increase, to provide additional strength, and to increase friction between insert 140 and head 104 to thereby decrease a likelihood of insert 140 backing out of engagement with head 104. A thickness of threads 114 and or 144 in this embodiment is characterized by an increased width measured along an axis lying along a direction of insertion of insert 140, as indicated by region "B" in FIGS. 1A and 5.

Referring again to enlarged view FIG. 1A, and to FIG. 3A, to further increase friction between an inserted or seated insert 140 and head 104, and to expand head 104 from a resting maximum dimension to an expanded maximum dimension, an interference fit is advantageously formed between an upper external diameter 146 of insert 140 and an upper internal diameter of head 104. The interference fit operates to force tabs 112 outwardly to increase a maximum dimension of head 104, due to introducing an increased overall diameter of insert 140 at external diameter 146. A bevel or chamfer may be provided adjacent to respective areas 116, 146 to promote smooth formation of the interference fit. It should be understood that an interference fit may be similarly formed anywhere along a mating interface between insert 140 and head 104.

Additionally, threads 144 may be provided with a ramped or an increasing diameter, or increasing thread height. Thread 114, 144 height in this embodiment is measured radially with respect to an axis of rotation of insert 140, as indicated by region "C" of FIGS. 1A and 5. Initially, a reduced thread diameter enables head 104 to conform to a compressed dimension when insert 140 is inserted within head 104, as illustrated by arrows "D" in FIG. 3, and as described more fully below. Additionally, an increasing diameter of threads 144 may operate to force tabs 112 outwardly to increase a maximum dimension of head 104, due to an increasing overall diameter of insert 140 as taller thread 144 areas are engaged, as insert 140 enters further into head 104. Alternatively or in addition to an increasing height of threads 144, threads 114 of head 104 may be provided with an increasing height, with like results. Accordingly enlarging of head 104 to form a secure engagement with implant 200 may be created by either engagement areas 116, 146, threads 114, 144, or both.

Head 104 may be provided with a gapped region 118 free of threads, sized to enable unrestricted passage of threads 144 of insert 140, whereby when insert 140 is fully seated, as shown in FIG. 3, insert 140 may rotate freely. In this manner, excessive tightening of insert 140 may be prevented.

Slight or limited resistance to insertion of head 104 into aperture 202 may be created by providing a reduced dimension "A" along a portion of aperture 202, for example at the region indicated by arrows "A" in FIG. 1. The reduced dimension "A" is smaller than the resting maximum dimension of head 104, thereby forming an interference fit. Accordingly, during insertion, tabs 112 deflect radially inwards towards a central longitudinal axis of fastener 100, due to engagement with the reduced dimension "A", thereby creating a compressed dimension of head 104 enabling transmission of head 104 past reduced dimension "A". Depending upon the desired degree of interference, a tactile and or audible feedback may be provided for a slight interference, or substantial force may be required, substantially contributing to a resistance to backing out of fastener 100. A tactile or audible feedback is created by expansion of head 104 from a compressed state to a resting or expanded state, and may be due in part to portions of head 104 striking implant 200 during this expansion.

To enable polyaxial movement, head 104 may be provided with a curved outer surface mateable with a curved inner surface 220 of aperture 202. The curved surfaces 120, 220 advantageously conform after head 104 has been expanded to a maximum expanded dimension, thereby maximizing an area of engagement between respective surfaces 120, 220. Surfaces 120, 220 may advantageously be provided with a texture or coating which enhances friction and improves a frictional bond between head 104 and aperture 200. In addition to, or in lieu of tactile feedback, insert 200 may be provided with one or more colored rings, or printed or etched markings, along area 146, to provide a visible indicator of a depth to which insert 200 has been driven into head 104. For example, a colored or marked portion may be obscured to indicate sufficient depth.

In use, implant 200 is positioned in a therapeutic location in the body, and body tissue is approximated or otherwise positioned to be stabilized. Insert 140 may be loosely positioned within head 104, or may be inserted later. If pre-positioned, a driving tool (not shown) is passed through insert 140 and into a mating recess or tool engagement 108 in fastener 100. Fastener 100 may be positioned through aperture 104 before or after connecting a tool, after which the tool is used to engage fastener 100 with body tissue. If insert 140 has not yet been assembled into head 104, it is advantageously assembled before head 104 passes reduced dimension "A" along a portion of aperture 202, but may also be assembled after. A driving tool is then used to complete engagement of fastener 100 with body tissue, after which the tool is withdrawn from direct engagement with head 104, but may be left in engagement with a tool engagement profile 148 of insert 140. It is not a requirement that the same tool drive insert 140, although it may reduce installation time if profile 148 is so configured. Insert 140 is then rotated to expand head 104 as described above, thereby securing fastener 100 with respect to implant 200.

Figure 8:
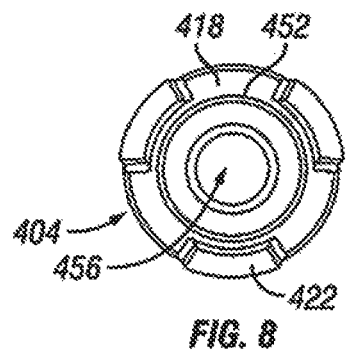
FIG. 8 depicts a top view of the anchor extension of FIG. 7.
Figure 9:
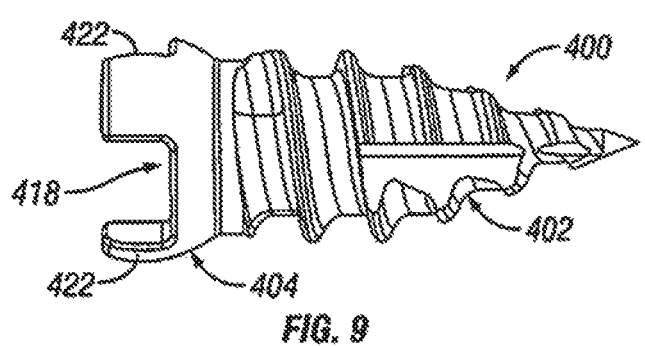
FIG. 9 depicts a side view of a fastener including the anchor extension of FIG. 7 and an anchor portion.
Figure 10:
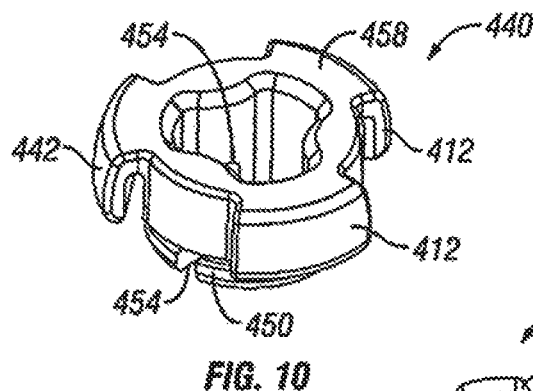
FIG. 10 depicts a perspective view of an insert connectable to the anchor extension of FIG. 7.
Figure 11:
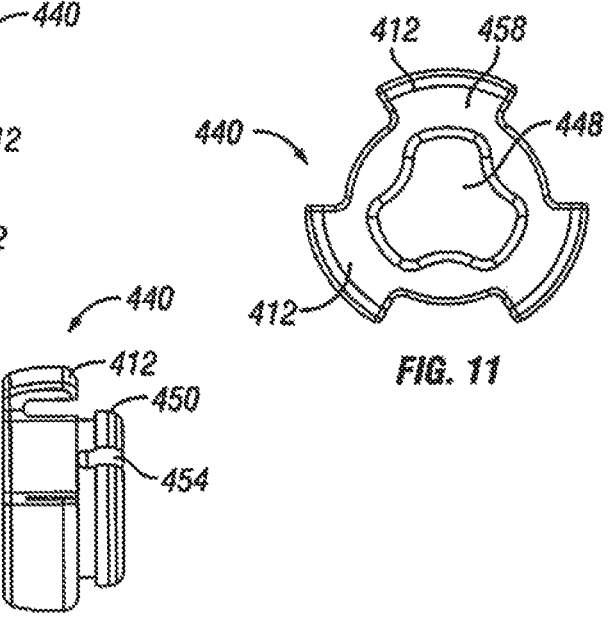
FIG. 11 depicts a top view of the insert of FIG. 10.
Figure 12:
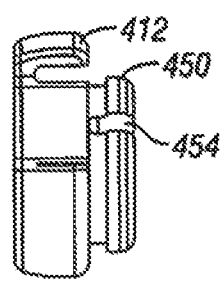
FIG. 12 depicts a side view of the insert of FIG. 10.

Referring now to FIGS. 7-15, an alternative fastener 400 has flexible tabs 412 positioned upon insert 440. Head 404 extends from anchor portion 402, and is provided with gapped regions 418 sufficiently wide to render a maximum resting dimension of head 404 substantially smaller than if gapped regions 418 were not present. In this manner, head 404 may be inserted into aperture 202, and may pass reduced dimension "A" along a portion of aperture 202, without a requirement of deflection of the ungapped circumferential portions 422 of head 404.

At least one of tabs 412 of insert 440 are sized and dimensioned to occupy gapped regions 418 of head 404. Insert 440 is positionable upon head 404, and has a relaxed maximum dimension that is larger than reduced dimension "A" along a portion of aperture 202; accordingly, the mated combination of insert 440 and head 404 has a relaxed maximum dimension that is larger than dimension "A". Three gapped regions 418 and three tabs 412 are illustrated, although it should be understood that a different number of mating gaps and tabs may be provided while remaining within the spirit and scope of the disclosure.

As insert 440 is inserted into aperture 202, tabs 412 deflect radially inwards due to engagement with the reduced dimension "A", thereby creating a compressed dimension of insert 440, enabling transmission of insert 440 past reduced dimension "A". As with embodiment 100, 140, head 404 and insert 440 may be preassembled. In the embodiment of insert 440, however, a tool (not shown) directly engages insert 440 at tool engagement 448, and through interaction of tabs 412 and circumferential portions 422, drives fastener 400 through aperture 202 and into body tissue. Accordingly, insert 440 is advantageously preassembled into head 404.

To enhance retention of insert 440 upon head 404, an insert retainer 450 engages a head retainer 452, in this embodiment having a form of mating hook portions, at least one of which is resiliently deflectable to enable engagement. Retainers 450 and 452 are advantageously formed as portions of a circumference of insert 440 and head 404, respectively. As may be seen in FIGS. 10 and 12, insert retainer 450 is provided as a flange with a gapped region 454 which enables retainer 450 to resiliently bend or deflect to pass over retainer 452, although it should be understood that a similar gapped region 454 may alternatively or additionally be provided upon retainer 452.

Advantageously, assembly of insert 440 and head 404 produces sensed feedback, including for example an audible, visual, or tactile sensation. A colored band, printed marking, or etched marking may be provided upon retainer 450 and or 452 to indicate whether a proper mating assembly of insert 440 and head 404 has taken place. For example, the visible marking is obscured when proper assembly has occurred.

The embodiment of FIGS. 7-15 further illustrate that fastener embodiments of the disclosure may be provided with a canulation 456, through which a k-wire, drill, or other fastener or tool may be passed. Additionally, insert 440 is provided with a triangular tool engagement region, which provides for a positive and secure tool engagement, while providing additional protection against stripping of engagement 448, due to the larger and deeper tool engagement faces afforded by providing three primary engagement faces, as opposed to, for example, the six smaller faces that would be found in a hex engagement. Additionally, anchor 402 may be provided with self tapping or other cutting profile 424 or anchoring means as would be understood by one skilled in the art.

To enable polyaxial movement, head 404 and insert 440 may be provided with ramped or curved outer surfaces 422, 442, respectively, mateable with a curved inner surface 220 of aperture 202. The curved surfaces 422, 442 advantageously conform to curve 220 after the assembly 404, 440 has been inserted into aperture 220, and after tabs 412 have been expanded to a maximum expanded dimension, thereby maximizing an area of engagement between respective surfaces 442, 422, and 220. Surfaces 422, 442, and or 220 may advantageously be provided with a texture or coating which enhances friction and improves a frictional bond between head 404, insert 440, and aperture 200. In addition to, or in lieu of tactile feedback, head 404 and or insert 440 may be provided with one or more colored rings, or printed or etched markings along areas 412, 442, respectively, to provide a visible indicator of a depth to which an assembly 404, 440 has been driven into aperture 202. For example, a colored or marked portion may be obscured to indicate sufficient depth.

With reference to FIGS. 15 and 15A, a terminating ledge 426 abuts an underside 428 of tab 412. If fastener 400 becomes loose, backs out, or is otherwise forced backwards out of aperture 202, ledge 426 will contact underside 428 and urge tabs 412 into engagement with curved inner surface 220 of aperture 202, thereby resisting backing out of fastener 200. In particular, during insertion, reduced dimension "A" applies a compressive force at an end of tab 412 which is distal from a point of attachment, or hinge 458, and therefore there is substantial bending leverage obtained due to the length of tab 412. A force to back out fastener 400, however, causes hinge 458 to be acted upon at dimension "A" directly, without benefit of leverage, and therefore fastener 400 cannot, as a practical matter, be forced out, absent application of a tool (not shown). For example, a tool may be provided which connects to head 404 or anchor 402 at a location apart from tab 412, and which has a component which is moveable relative to the connection, for example a threadably attached ring, which may be caused to bear upon tabs 412 to operate hinge 458 to reduce a maximum dimension of fastener 400, thereby enabling removal.

In an alternative embodiment shown in FIG. 15A, representing an enlarged and alternative rendering of a portion of FIG. 15, ledge 426A and underside 428A are provided with complementary angled slopes which further urge tabs 412 into engagement with inner surface 220, in response to a reversing force acting upon fastener 400.

A further embodiment is illustrated in FIGS. 16-25, in which head 604 extends from anchor portion 602, and is provided with a tapered surface 630, cooperative with a mating tapered surface 650 of insert 640. In this embodiment, insert 640 is positioned about an outer surface of head 604, and engages curved surface 220 of implant 200 along a complementary curved surface 642. Insert 640 forms resilient tabs 612 separated by insert reliefs 610. In this embodiment, reliefs 610 are formed upon alternating faces of insert 640, thereby forming hinges 658, enabling a diameter of insert 640 to enlarge and reduce.

With reference to FIGS. 18 and 20, in particular, head 604 is provided with a retainer 652 operative to retain insert 640 in engagement with head 604. In the embodiment of FIGS. 16-25, retainer 652 is formed as an integral flange disposed along an upper circumference of head 604, although retainer 652 may be separately attached. Insert 640 advantageously has a retainer 654 that is formed as a ledge or cooperating shape with respect to retainer 652, whereby retainers 652 and 654 are thereby adapted to abut and or mate and thereby resist the passage of one over or under the other.

To assemble insert 640 onto head 604, insert 640 is passed over retainer 652, insert 640 expanding through bending of hinges 658, and after passing completely over retainer 652, resiliently resuming a former relaxed shape with a smaller diameter, and becoming thereby prevented from separating from head 604. The assembled head 604 and insert 640 may thereafter be assembled into aperture 202 by inserting the assembly past reduced dimension "A" along a portion of aperture 202, as described more fully below.

With reference to FIG. 20, insert 640 defines an insertion or leading end 660 and a trailing end 662. A first ramped surface "E" extends from leading end 660 and has a generally increasing diameter along an axis extending from leading end 660 in a direction of trailing end 662. A second ramped surface extends from trailing end 660 and has a generally increasing diameter along an axis extending from trailing end 660 in a direction of leading end 660. Ramp "F" has a steeper or more rapidly increasing diameter than shallower ramp "E". Ramps "E" and "F" advantageously, but not necessarily, extend circumferentially about insert 640. Ramped surfaces "E" and "F" matingly engage curved surface 220, thereby enabling polyaxial movement of fastener 600.

During insertion into aperture 202, insert 640 is initially urged by engagement with dimension "A" away from anchor 602 towards an end of head 604, until further movement is arrested by retainer 652. Subsequently, ramp "E" of outer surface 642, and curved surface 220, slide in mutual engagement, creating pressure which causes a contraction of insert 640, bending hinges 658 to reduce a diameter of insert 640, whereby insert 640 together with head 604 are sized to be passable through dimension "A".

After the assembled head 604 and insert 640 lie within aperture 202, curved inner surface 220 and curved outer surface 642 of insert 640 cooperate to prevent fastener 600 from backing out. More particularly, as fastener 600 moves in a direction reversed with respect to an insertion direction, insert 640 moves towards anchor 602 and advances along tapered surface 630, whereupon ramp "E" becomes wedged or pinched between curve 220 and tapered surface 630 of head 604, binding insert 640 against head 604 with increasing force, and progressively preventing further backing out of fastener 600. Should ramp "F" be driven against reduced dimension "A" at any time, the steep angle of ramp "F" is blocked by reduced dimension "A", and implant 640 is further driven into the aforedescribed wedged configuration.

To enable polyaxial movement, curved outer surfaces defined by ramps "E" and "F" advantageously cooperatively mate or conform to curved inner surface 220 of aperture 202. Surfaces 642 and or 220 may advantageously be provided with a texture or coating which enhances friction and improves a frictional bond between head 604, insert 640, and aperture 200. In addition to, or in lieu of tactile feedback, head 604 and or insert 620 may be provided with one or more colored rings, or printed or etched markings upon surface 642 respectively, to provide a visible indicator of a depth to which an assembly 604, 640 has been driven into aperture 202. For example, a colored or marked portion may be obscured to indicate sufficient depth.

Fasteners 100, 400, 600 of the disclosure may inserted or screwed into body tissue at any desired angle, and therefore need not be inserted perpendicular to a surface of implant 200. The curved or spherical properties of head 104, 404, 604, including a combination with implant 440 or 640 and the spherical curvature of aperture 200, cooperate to reduce the incidence of a fastener of the disclosure from backing out. More particularly, the largest diameter of the head of the screw is larger than the diameter of the narrowest portion of the opening in the top our outer side of implant 200, through which the screw head has been placed.

The extent of interference between the fastener head diameter and the narrow opening (diameter "A") may be different depending on the size of the plate, openings, and fastener heads being used. For example the interference difference between the fastener head and the narrowest opening of implant 200 may be about 0.01 mm or greater, about 0.03 mm or greater, or about 0.10 or greater, or even about 0.20 mm or greater. Alternatively, the interference between the fastener head and the narrow outer opening may be described relative to the outer diameter of the fastener head itself. For example, the interference may be about 0.5% or greater of the diameter of the fastener head, about 5% or greater of the diameter of the fastener head, or even about 10% or greater of the outer diameter of the fastener head. Advantageously, the interference is less than about 40% of the outer diameter of the fastener head, for increased reliability and strength.

While an incidence of backing out is prevented or reduced in likelihood in accordance with the disclosure, rotation of anchor 100, 400, 600 within aperture 202 is not prevented. One advantage of allowing the fastener to rotate freely is that the implant, for example a bone fixation plate, is able to accommodate for movements in the bones, for example the vertebrae, and to or accommodate for compression of any bone grafts that have been placed between stabilized bones. An advantage of allowing the screws to be inserted at any angle is that a relatively close spacing of the screws is enabled, without the risk of mutual interference.

During insertion, when a fastener head of the disclosure interferes with an implant of the disclosure at an interference point, a slight resistance is generated relative to a backing out force. The available force of insertion easily overcomes this resistance. When the fastener is advanced past an interference point, a snap may be perceived as the fastener head moves into a sliding fit area and is allowed to expand and move more freely. The forces which can cause a fastener to back out from the implant are advantageously insufficient to pass the fastener head back past the interference section. In an embodiment, a set screw may be used to further prevent backout of the fastener. In other embodiments, the head of the fastener may be separately clamped to prevent rotation, when such a restriction on the movement of the fastener is desirable.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method of securing body tissue relative to an implant comprising:
    positioning an implant having an aperture having a first diameter adjacent to a bone member;
    inserting a fastener having a head portion and an anchor portion into the aperture such that the anchor portion is inserted into the bone member and the head portion is retained in the aperture, wherein the head portion comprises one or more gapped regions that are cut through an upper surface of the head portion, wherein the head portion has a first diameter, the first diameter of the head portion is equal to or smaller than the first diameter of the aperture such that the head portion does not deflect when being inserted into the aperture; and
    an insert positioned within an opening in the head portion of the fastener, wherein the insert includes one or more tabs, each of which at least partially occupies the one or more gapped regions such that the one or more tabs are at least partially positioned in the one or more gapped regions in the locked position, wherein the insert has a first diameter, the first diameter of the insert being equal to or larger than the first diameter of the aperture such that at least one of the tabs will deflect inwardly when inserted into the aperture.

2. The method of claim 1, wherein the insert further comprises an insert retainer that engages a head retainer of the head portion of the fastener, and wherein the insert retainer comprises a flange with a gapped region which enables the insert retainer to resiliently bend or deflect to pass over the head retainer.

3. The method of claim 1, wherein at least a portion of the head portion has a second diameter and at least a portion of the insert has a second diameter, the second diameter of the head portion being smaller than the second diameter of the insert.

4. The method of claim 1, wherein the one or more tabs extend the entire length and width of the one or more gapped regions.

5. The method of claim 1, wherein the insert is positioned in an unlocked position when the one or more tabs are not positioned in the one or more gapped regions.

6. The method of claim 1, wherein the one or more tabs of the insert are flexible.

7. The method of claim 1, wherein the insert is preassembled into the head portion of the fastener.

8. The method of claim 7, wherein the insert is compressed as the insert passes through the aperture of the implant.

9. The method of claim 8, wherein the insert expands after the insert is compressed as the insert progresses further downward into the aperture.

10. The method of claim 1, wherein the insert has an upper diameter that is greater than a lower diameter of the insert.

11. The method of claim 10, wherein the upper diameter is provided by increasing a thread height of threads that extend around the insert.

12. The method of claim 1, wherein the insert comprises outer threads and the head portion of the fastener comprises inner threads that engage the outer threads.

13. A method for preventing back out of a fastener comprising:
    positioning a plate member having an aperture having a first diameter against a bone member;
    inserting a fastener having a head portion and an anchor portion into the aperture, wherein the anchor portion is inserted into the bone member and the head portion is engaged with the plate, wherein the head portion comprises one or more gapped regions that are cut through an upper surface of the head portion, and wherein the one or more gapped regions extend circumferentially around the head portion of the fastener, wherein the head portion has a first diameter, the first diameter of the head portion is equal to or smaller than the first diameter of the aperture such that the head portion does not deflect when being inserted into the aperture; and
    moving an insert positioned in an opening in the head portion of the fastener to a locked position, wherein the insert includes one or more tabs, each of which occupies the one or more gapped regions such that the one or more tabs are inserted into the one or more gapped regions in the locked position, wherein the insert has a first diameter, the first diameter of the insert being equal to or larger than the first diameter of the aperture such that at least one of the tabs will deflect inwardly when inserted into the aperture.

14. The method of claim 13, wherein the insert further comprises an insert retainer that engages a head retainer of the head portion of the fastener, and wherein the insert retainer comprises a flange with a gapped region which enables the insert retainer to resiliently bend or deflect to pass of the head retainer.

15. The method of claim 13, wherein the one or more tabs of the insert are flexible.

16. The method of claim 13, wherein the insert comprises threads and the head portion of the fastener comprises threads that engage one another.

17. The method of claim 13, wherein the insert has an upper diameter that is greater than a lower diameter of the insert.

18. The method of claim 17, wherein at least a portion of the insert is ramped or tapered to create the different diameters.

19. The method of claim 13, wherein two or more tabs are compressed as the insert is inserted through the aperture of the implant.

20. The method of claim 19, wherein the one or more tabs expand following compression as the insert is inserted further down the aperture of the implant.

* * * * *